United States Patent [19]

Bolton

[11] Patent Number: 5,591,457

[45] Date of Patent: Jan. 7, 1997

[54] METHOD OF INHIBITING THE AGGREGATION OF BLOOD PLATELETS AND STIMULATING THE IMMUNE SYSTEMS OF A HUMAN

[75] Inventor: Anthony E. Bolton, Sheffield, England

[73] Assignee: Vasogen Inc, Etobicoke, Canada

[21] Appl. No.: 352,802

[22] Filed: Dec. 1, 1994

Related U.S. Application Data

[63] Continuation of Ser. No. 941,327, Sep. 4, 1992, abandoned, which is a continuation-in-part of Ser. No. 832,798, Feb. 7, 1992, abandoned.

[51] Int. Cl.$^6$ .............................. A01N 1/00; A61K 33/00; A61L 2/10
[52] U.S. Cl. .................... 424/613; 424/810; 514/929; 422/24; 422/44; 422/45; 422/46; 604/4; 435/2
[58] Field of Search .................................. 424/613, 810; 422/45, 24, 44, 46; 250/493.1; 604/4; 514/929; 435/2

[56] References Cited

U.S. PATENT DOCUMENTS

| | | | |
|---|---|---|---|
| 695,657 | 3/1902 | Smith | 604/25 |
| 3,715,430 | 2/1973 | Ryan | 424/127 |
| 3,925,344 | 12/1975 | Mazur | 530/385 |
| 4,061,736 | 12/1977 | Morris et al. | 514/6 |
| 4,473,496 | 9/1984 | Scannon | 530/385 |
| 4,500,534 | 2/1985 | Frehel et al. | 514/301 |
| 4,529,719 | 7/1985 | Tye | 514/6 |
| 4,584,130 | 4/1986 | Bucci et al. | 530/385 |
| 4,600,531 | 7/1986 | Walder | 123/456 |
| 4,632,980 | 6/1990 | Zee et al. | 530/380 |
| 4,659,726 | 4/1987 | Yoshino et al. | 514/365 |
| 4,826,811 | 5/1989 | Sehgal et al. | 514/6 |
| 4,831,268 | 5/1989 | Fisch et al. | 250/432 |
| 4,857,636 | 8/1989 | Hsia | 530/385 |
| 4,968,483 | 11/1990 | Müeller et al. | 422/45 |
| 4,983,637 | 1/1991 | Herman | 514/724 |
| 5,028,588 | 7/1991 | Hoffman et al. | 514/6 |
| 5,052,382 | 10/1991 | Wainwright | 128/202 |
| 5,194,590 | 3/1993 | Sehgal et al. | 530/385 |
| 5,250,665 | 10/1993 | Kluger et al. | 530/385 |

OTHER PUBLICATIONS

Medline Abstract 91104111, abstracting: Petukhov, E. B. et al. "Correction of Blood Hyperviscosity . . . " Grud Seroechnososudistaia Khir, (1990) (10), pp. 34–37.

Medline Abstract 90020932, abstracting: Petukhov, E. B. et al. "Decreased Activity of Lipid . . . " Vestn Khir (May 1989), vol. 142(5), pp. 36–39.

Medline Abstract 80130497, abstracting: Vella Briffa D. et al. "Inhibition of human blood platelet aggregation . . . " Br. J. Dermatol. (1979 Dec.), vol. 101(6), pp. 679–683.

Drug Facts and Comparisons, 1994 edition, published by Facts and Comparisons, St. Louis, see pp. 263–269.

Cecil Textbook of Medicine, 19th ed., published by W. B. Saunders Co., PA, 1992, pp. 253–269, 823, 1085, 1530–1534 and 2161.

Physicians' Desk Reference, 47th ed., published by Medical Economics Data, NJ, 1993, pp. 710 and 2408–2411.

Rook, Alain H. et al., "Treatment of Autoimmune Disease with Extracorporeal Photochemotherapy: progressive systemic sclerosis," The Yale J. of Biology and Medicine, vol. 62, No. 6, Nov./Dec. 1989, pp. 639–645.

Tattoni, G. et al., "Osservazioni sull'efficacia di un trattamento balneoterapico ozonizzato in pazienti affetti da vasculopatie periferiche," Minerva Cardioangiologica, vol. 25/9, 1977, pp. 745–748.

"Cloned and Expressed Nitric Oxide Synthase Structurally Resembles Cytochrome P–450 Reductase," *Nature*, Jun. 27, 1992, vol. 351, pp. 714–718.

*British Medical Journal*, vol. 296, Jan. 30, 1988, pp. 320–331, entitled "Secondary Prevention of Vascular Disease by Prolonged Antiplatelet Treatment".

"Ozone: Historical Review," published in *Biomedical Technology*, Dec. 16, 1991, p. 5.

"Biological Roles of Nitric Oxide," *Scientific American*, May 1992, pp. 68–77.

D. Baran et al (associates) "Technical Report and Clinical Update" Mueller Medical International Inc., Oakville, Ontario, Canada, Sep. 1990.

Primary Examiner—John Pak
Attorney, Agent, or Firm—Ridout & Maybee

[57] ABSTRACT

A method of inhibiting the aggregation of blood platelets in a human, which comprises: (a) contacting from about 0.01 ml to about 400 ml of blood with a blood platelet aggregation-inhibiting effective amount of ozone gas and ultraviolet radiation; and (b) administering the blood treated in step (a) to a human. A method of stimulating the immune system, and of treating immune system disorders, by treating blood with ultraviolet radiation and ozone gas, followed by administering the treated blood to a human.

Also disclosed is a method of treating Raynaud's Disease by contacting about 0.01 ml to about 400 ml of human blood with a blood platelet aggregation-inhibiting effective amount of ozone gas in admixture with oxygen gas, and ultraviolet radiation, while maintained at a temperature in the range of from about 37° C. to about 43° C. for a period for about 0.5 minutes to about 10 minutes, and administering the blood so treated to a human patient with Raynaud's Disease.

9 Claims, No Drawings

METHOD OF INHIBITING THE AGGREGATION OF BLOOD PLATELETS AND STIMULATING THE IMMUNE SYSTEMS OF A HUMAN

CROSS-REFERENCE TO RELATED APPLICATIONS

This application is a continuation of U.S. patent application Ser. No. 07/941,327, filed Sep. 4, 1992, now abandoned; which is a continuation-in-part of U.S. patent application Ser. No. 07/832,798, filed Feb. 7, 1992, now abandoned, the entire disclosure of which is incorporated herein by reference.

BACKGROUND OF THE INVENTION

1. Field of the Invention

The present invention relates to a method of inhibiting blood platelet aggregation in humans, as well as to a method of therapeutically treating human disease conditions associated with blood platelet aggregation. The invention also pertains to a method of stimulating the immune system, and to a method of therapeutically treating immune system disorders.

2. Description of the Prior Art

Platelets are the smallest of the formed elements of the blood. Every cubic millimeter of blood contains about 250 million platelets, as compared with only a few thousand white cells. There are about a trillion platelets in the blood of an average human adult. Platelets are not cells, but are fragments of the giant bone-marrow cells called megakaryocytes. When a megakaryocyte matures, its cytoplasm breaks up, forming several thousand platelets. Platelets lack DNA and have little ability to synthesize proteins. When released into the blood, they circulate and die in about ten days. However, platelets do possess an active metabolism to supply their energy needs.

Because platelets contain a generous amount of contractile protein (actomyosin), they are prone to contract much as muscles do. This phenomenon explains the shrinkage of a fresh blood clot after it stands for only a few minutes. The shrinkage plays a role in forming a hemostatic plug when a blood vessel is cut. The primary function of platelets is that of forming blood clots. When a wound occurs, platelets are attracted to the site where they activate a substance (thrombin) which starts the clotting process. Thrombin, in addition to converting fibrinogen into fibrin, also makes the platelets sticky. Thus, when exposed to collagen and thrombin, the platelets aggregate to form a plug in the hole of an injured blood vessel.

Platelets not only tend to stick to one another, but to the walls of blood vessels as well. Because they promote clotting, platelets have a key role in the formation of thrombi. The dangerous consequences of thrombi are evident in many cardiovascular and cerebrovascular disorders.

In this regard, the precise function of blood platelets in various human disease states has recently become increasingly understood as advances in biochemistry permit the etiologies of diseases to be better understood.

For example, many attempts have been made to explain the process of atherogenesis, that is, the creation of plaque which narrows arteries and, of particular concern, the coronary arteries. Recently, there has been increasing interest in the possible role of platelets in atherosclerosis.

In addition, a number of disease states in humans are believed to be associated with an aggregation of platelets in the blood. These platelet aggregation associated conditions include: peripheral vascular disease; thrombotic diseases such as coronary thrombosis and pulmonary thrombosis; stroke; eclampsia and pre-eclampsia; and hypertension.

A study completed by the University of Oxford, England, and published in the British Medical Journal, Vol. 296, Jan. 30 1988, pages 320–331, entitled "Secondary Prevention of Vascular Disease by Prolonged Antiplatelet Treatment," suggests that therapies which inhibit platelet aggregation may be useful for treating occlusive vascular disease. The study utilized aspirin, sulphinpyrazone, or aspirin and dipyridamole as the platelet aggregation inhibiting agents.

Unfortunately, long-term aspirin therapy may lead to severe gastrointestinal irritation and bleeding. Also, these and other known agents which inhibit platelet aggregation may have other undesirable side-effects that make them unsuitable for administration to patients who could benefit from such therapy. For pregnant women with pre-eclampsia or other platelet aggregation associated conditions, the administration of drugs may be undesirable in view of the potential effects of the same on the developing fetus.

It would therefore be desirable to provide a method of inhibiting blood platelet aggregation which overcomes the deficiencies of the prior art.

A separate body of prior art discloses various methods of using ozone gas to treat certain human diseases, wounds and infections:

U.S. Pat. No. 695,657 to Smith discloses a portable ozonizer for the treatment of wounds. The device includes an ozonizer housed in a glass jacket, one end of which receives an air-supply tube and other end of which functions as an outlet tube for the ozonized air. The device enables topical application of ozone gas, which is said to be used to treat suppurating or gangrenous surfaces.

U.S. Pat. No. 3,715,430 to Ryan relates to a method and apparatus for producing substantially pure oxygen having a controlled content of ozone and higher oxygen polymers. The purified oxygen gas is exposed to ultraviolet light in a wavelength of 2485 to 2537 angstrom units in order to produce 5 to 500 parts per million of ozone and higher oxygen polymers in the gas mixture. Ryan indicates that the gas produced in this manner is non-irritating to the human body and may be intravenously injected into the blood stream for therapeutic use.

U.S. Pat. No. 4,632,980 to Zee et al. discloses a method of freeing blood and blood components of enveloped viruses by contacting the blood or blood product in an aqueous medium with an enveloped virus inactivating amount of ozone. The treatment is carried out at a temperature of 4° to 37° C., and an ozone concentration of 1–100 ppm. The disclosed process is said to useful for inactivating the hepatitis virus, HTLV-I, -II, and -III, and influenza virus.

U.S. Pat. No. 4,831,268 to Fisch et al. provides a method for the radiation of corporeal blood to prevent arteriosclerosis related heart and vascular diseases caused by disturbances in the fat exchange. The disclosed process involves irradiating the blood in a blood conducting tube with radiation having an intensity of from about 1 mWcm$^{-2}$ to 10 mWcm$^{-2}$ in a wavelength range of from about 320 nm to 600 nm.

U.S. Pat. No. 4,968,483 to Müller et al. discloses an apparatus for the production of oxygenated blood. The apparatus includes a vessel for containing the blood to be processed, an ultraviolet lamp and infrared lamp associated with the vessel, and a feed pipe extending into the vessel to a position near the bottom of the vessel, in which the feed pipe is connected to a source of ozone.

U.S. Pat. No. 4,983,637 to Herman relates to a method of treating systemic viral infections by the parenteral administration of pharmacologically effective amounts of ozonides of terpenes in pharmaceutically acceptable carriers. The disclosed method is particularly directed to the treatment of HIV infections.

U.S. Pat. No. 5,052,382 to Wainwright discloses an apparatus for the controlled generation and administration of ozone. The apparatus includes a generator for generating ozone, a monitor for monitoring the ozone production, a dosage device for providing a predetermined amount of ozone administration, and a computer control device for controlling the operation of the apparatus. The patent further discloses that administration of ozone to patients is known for the treatment of viral and bacterial infections, as well as for the treatment of external sores and wounds.

SUMMARY OF THE INVENTION

Applicant has discovered that the aggregation of blood platelets in a human may be inhibited by contacting from about 0.01 ml to about 400 ml of blood from a human with a blood platelet aggregation-inhibiting effective amount of ozone gas and ultraviolet radiation, followed by administering the treated blood to a human.

The method of the invention is contemplated to be useful in treating a variety of conditions in humans which are associated with blood platelet aggregation such as arterial occlusive diseases, including peripheral vascular disease; thrombotic diseases, such as coronary thrombosis, pulmonary thrombosis, arterial thrombosis, and venous thrombosis; circulatory disorders, such as Raynaud's disease; stroke; pre-eclampsia; and hypertension.

The method of the invention increases blood levels of nitric oxide, which may partly explain the effect of inhibiting platelet aggregation achieved by the invention. Additionally, treatment of blood with ultraviolet radiation and ozone gas according to the invention has been found to increase blood levels of prostacyclin, a substance which is known to inhibit platelet aggregation and relax peripheral blood vessels.

The inventive method of treating blood has also been unexpectedly found to activate the human immune system by stimulating T-lymphocytes and monocytes, and by increasing the potential of peripheral blood mononuclear cells to proliferate. Thus, the invention also contemplates a method of treating immune system disorders by contacting from about 0.01 ml to about 400 ml of blood from a human with an immune system-stimulating effective amount of ozone gas and ultraviolet radiation, followed by administering the treated blood to a human.

DETAILED DESCRIPTION OF THE INVENTION

The present invention provides a method of inhibiting the aggregation of blood platelets in a human, which comprises:

(a) contacting from about 0.01 ml to about 400 ml of blood with a blood platelet aggregation-inhibiting effective amount of ozone gas and ultraviolet radiation; and (b) administering the blood treated in step (a) to a human.

As evidenced by the data set forth in Examples 1 and 2 below, Applicant has found that satisfactory inhibition of platelet aggregation can only be achieved when the blood is treated with a combination of ozone gas and ultraviolet radiation. Treatment of blood solely with ozone gas produces minimal inhibition of blood platelet aggregation. Moreover, treatment of blood solely with ultraviolet light produces no inhibition of platelet aggregation whatsoever.

The combined treatment with ozone gas and ultraviolet light, however, has unexpectedly been found to produce significant inhibition of blood platelet aggregation, which may be useful in treating a variety of disorders associated with blood platelet aggregation.

The term "aggregation of blood platelets" as used herein refers to the sticking together of platelets to other platelets and/or to the walls of a blood vessel.

The ozone gas may be provided by any conventional source known in the art, such as an ozonizer. The ozone gas used in connection with the inventive method has a concentration of ozone of from about 0.5 µg/ml to about 100 µg/ml. Preferably, the ozone gas has a concentration of from about 5 µg/ml to about 50 µg/ml. The ozone gas is preferably delivered to the blood by means of a medical oxygen carrier; the ozone gas is preferably contacted with the blood by any means known in the art, preferably by bubbling the ozone/oxygen mixture through the blood sample.

The ultraviolet radiation may be provided by any conventional source known in the art, for example by a plurality of low-pressure ultraviolet lamps. The invention preferably utilizes a standard UV-C source of ultraviolet radiation. Preferably employed are low-pressure ultraviolet lamps that generate a line spectrum wherein at least about 90% of the radiation has a wavelength of about 253.7 nm. It is believed that ultraviolet radiation having emission wavelengths corresponding to standard UV-A and UV-B sources would also provide acceptable results.

The blood to be treated with UV/ozone is preferably heated to a temperature of from about 0° C. to about 56° C. while being contacted with the ozone gas and ultraviolet radiation. Any suitable source of heat known in the art may be employed to heat the blood, preferably one or more infrared lamps. The blood may be heated to about 37°–43° C., most preferably about 42.5° C. prior to being contacted with the ozone gas and ultraviolet radiation. Preferably, the temperature of the blood is then maintained at about 42.5° C. during the treatment with UV/ozone.

Alternatively, the blood sample is heated while being subjected to UV radiation, until the blood reaches a predetermined temperature (preferably about 42.5° C.), at which point bubbling of ozone gas through the blood is commenced. The concurrent UV/ozone treatment is then maintained for a predetermined period of time, preferably about 3 minutes.

Another alternative method involves subjecting the blood to UV/ozone while heating to a predetermined temperature (preferably about 42.5° C.), then either ending the treatment once the predetermined temperature is reached, or continuing UV/ozone treatment for a further period of time, most preferably about 3 minutes.

Heating the blood to about 42.5° C. with the infrared lamps preferably employed according to the invention has been found to take from about one minute and fifty seconds to about two minutes and ten seconds.

It will be understood that the source of blood treated according to the invention may be blood from an outside source, such as a blood donor of compatible blood type, which is treated with UV/ozone and then administered to a patient. Alternately, and preferably, the blood to be treated may be withdrawn from the human patient as an aliquot, treated with UV/ozone, then readministered to the patient from whom the aliquot of blood was taken. All or a portion of the blood removed from the patient may be treated and then readministered to the patient.

In general, from about 0.01 ml to about 400 ml of blood may be treated according to the invention. Preferred amounts are in the range of about 0.1 ml to 200 ml, and more preferably from about 1 ml to 50 ml of blood. The method most preferably involves treating about 10 ml of blood with ozone gas and ultraviolet radiation, then administering (or readministering) the treated blood to the patient by intramuscular injection.

Other conventional techniques known in the art for administering blood may be employed, such as inter-arterial injection, intravenous injection, subcutaneous injection, and intraperitoneal injection. The administration of small volumes of host blood in this fashion is termed micro-autohemotherapy.

The invention also contemplates an embodiment wherein blood is continuously removed from a patient's body and circulated through an apparatus which treats the blood with ozone gas and ultraviolet light as described above, before returning the blood to the patient. This procedure would have particular utility, for example, during the performance of operative procedures, such as coronary bypass surgery.

The blood is contacted with the ozone gas and ultraviolet radiation for a period of time sufficient to effectively inhibit the aggregation of blood platelets. A treatment period of from a few seconds to about 60 minutes, preferably from about 0.5 minutes to about 10 minutes, and most preferably about 3 minutes, has been found to provide satisfactory inhibition of platelet aggregation. The blood is preferably maintained at a temperature of about 42.5° C. during the three minute treatment period.

The method should be carried out under sterile conditions known to those of ordinary skill in the art.

The method of the invention may be carried out using conventional apparatus for ozonating blood and irradiating blood with ultraviolet light known to those skilled in the medical art. Preferably, an apparatus similar to that disclosed in U.S. Pat. No. 4,968,483 is employed to carry out the method of the invention. The disclosure of U.S. Pat. No. 4,968,483 is incorporated herein in its entirety by reference.

In a preferred aspect of the invention, a method of inhibiting the aggregation of blood platelets in a human is provided, which comprises:

(a) contacting from about 0.01 ml to about 400 ml of blood from a human with a blood platelet aggregation-inhibiting effective amount of from about 5 µg/ml to about 50 µg/ml of ozone gas and ultraviolet radiation having a wavelength of about 253.7 nm, while maintaining the blood at a temperature of from about 37° C. to about 43° C.; and (b) administering the blood treated in step (a) to a human.

The invention also contemplates a method of treating a condition in a human associated with blood platelet aggregation, by contacting about 0.01 ml to about 400 ml of blood from a human with a blood platelet aggregation-inhibiting effective amount of ozone gas and ultraviolet radiation, followed by administering the treated blood to a human.

The useful and preferred ranges of ozone concentration, ultraviolet wavelength, temperature, and other parameters of the method of treatment are the same as described above with regard to the method of inhibiting blood platelet aggregation.

Those skilled in the art will appreciate that the method of inhibiting blood platelet aggregation provided by the invention will have therapeutic utility for treating a wide range of disease states associated with the aggregation of blood platelets in humans.

The term "treating" as used herein refers to the alleviation or prevention of a particular disorder. In the case of traumatic conditions such as stroke, preventative treatment is obviously preferred. Also, although the term "human" is used to describe the preferred host, those skilled in the art will appreciate that the methods of the invention would have similar utility with other mammals.

The following diseases are illustrative of known conditions which may be associated with the aggregation of blood platelets, and which are treatable according to the inventive method: arterial occlusive diseases including peripheral vascular disease; arterial and venous disorders including thrombotic diseases such as coronary thrombosis, pulmonary thrombosis, arterial thrombosis, and venous thrombosis; circulatory disorders, such as Raynaud's disease; stroke; pre-eclampsia; and hypertension. This list is merely illustrative of conditions which are associated with platelet aggregation; those of ordinary skill in the art will appreciate that other disease states associated with an aggregation of blood platelets may be treated with the inventive technique.

With regard to peripheral vascular disease, the disease could theoretically be explained by a reduction of endothelial-derived relaxing factor (EDRF), low levels of which lead to a contraction of the smooth muscle of blood vessels, and hence a reduction in the diameter of the lumen of the vessel and a reduction in blood flow. The major naturally occurring EDRF is nitric oxide. In addition, nitric oxide stabilizes blood platelets, reducing their aggregation. An increase in EDRF (nitric oxide) levels, therefore, has a double beneficial effect on the circulatory system: it inhibits aggregation of platelets, making the blood more fluid, and it enlarges the diameter of the vessels, improving the flow.

As illustrated in Example 2 below, the method of the invention is believed to increase nitric oxide levels in the blood, which may explain one mode of action in the inventive treatment of peripheral vascular disease and other conditions associated with blood platelet aggregation.

Pre-eclampsia may lead to eclampsia, an acute hypertensive crisis that may occur in the second or third trimester of pregnancy. Although the precise etiology is unknown, overactive platelet activity leading to the formation of thrombi in the placenta is believed to be a cause of the condition. The inventive method, which results in a stabilization of the patient's blood platelets and an inhibition of platelet aggregation, is therefore a potential treatment modality. In particular, the method of the invention may be preferred over conventional antiplatelet therapies, where the administration of drugs to the mother is counterindicated.

Example 3 below shows that the method of the invention increases the blood concentration of 6-keto prostaglandin-F1-alpha, the stable metabolite of prostacyclin which is used to measure prostacyclin levels. Prostacyclin is a substance produced by platelets which inhibits platelet aggregation and relaxes peripheral blood vessels. The increase in prostacyclin levels provided by the invention thus appears to be another mechanism whereby the method is effective for treating peripheral vascular disease, and the other disclosed conditions associated with platelet aggregation.

Prostacyclin has in the past been used as an experimental treatment for Raynaud's disease, which is a severe form of circulatory disorder affecting the extremities. Prostacyclin, however, is too unstable and expensive to be a commercially practicable therapeutic agent. The method of the invention therefore provides a more satisfactory means for treating circulatory diseases, such as Raynaud's disease, which are benefitted by an increase in blood levels of prostacyclin.

Examples 4 and 5 below support the finding that the method of treating blood according to the invention has an immune-stimulatory effect. In particular, treatment of blood with UV/ozone has been found to increase the proliferation of peripheral blood mononuclear cells after stimulation with Interleukin-2 (IL-2) (see Example 4), and also to stimulate T-lymphocytes and monocytes (see Example 5).

Thus, the invention also provides a method of stimulating or activating the immune system in a human by contacting about 0.01 ml to about 400 ml of blood from a human with an immune system-stimulating effective amount of ozone gas and ultraviolet radiation, followed by administering the treated blood to a human. Similarly, the invention contemplates a method of treating an immune system disorder in a human, by contacting about 0.01 ml to about 400 ml of blood from a human with an immune system-stimulating effective amount of ozone gas and ultraviolet radiation, followed by administering the treated blood to a human.

The useful and preferred ranges of ozone concentration, ultraviolet wavelength, temperature, and other parameters of these methods of treatment are the same as described above with regard to the method of inhibiting blood platelet aggregation.

The immune system disorders which may be treated by this method include allergic conditions, autoimmune conditions, and inflammatory conditions. Specific immune system disorders which may be treated according to the invention include arthritis, rheumatoid arthritis, asthma, graft-versus-host disease, diabetes mellitus, organ rejection, miscarriage, osteoarthritis, systemic lupus erythematosus, atopic allergy, multiple sclerosis, allergic dermatitis, inflammatory bowel disease, psoriasis, sarcoidosis, and other inflammatory disorders.

Further, the immune system disorder to be treated according to the present invention may be a lymphoproliferative disorder, such as malignant non-Hodgkin's lymphoma, Hodgkin's disease, or malignant histiocytosis. Also, the immune system disorder may be a neoplastic disorder, such as a leukemia.

The discoveries of the present invention may also be applied to test inflammatory and autoimmune diseases, and may be applied to treat autoimmune diseases manifested by infertility. The immune system disorder to be treated may be a disorder resulting from the presence in a human of the virus which causes acquired immunodeficiency syndrome (AIDS).

More generally, the treatment of an "immune system disorder" is contemplated to mean the treatment of any disease that is associated with a reduced activity of the immune system, or which may be benefitted by increasing the activity of the immune system. Thus, the process of the invention may find applicability in the treatment of a variety of infectious diseases, particularly viral infections such as the HIV virus, tumors, bacterial, yeast or protozoal infections, and the like.

The following examples are given to illustrate the invention but are not deemed to be limiting thereof.

EXAMPLE 1

Inhibition of Blood Platelet Aggregation

The following experiment was conducted to study the effects of ozone/ultraviolet light treatment on blood platelet activity.

Experimental Procedure

Samples (20 ml) of peripheral blood were taken from 10 individuals for 13 separate experiments. Each sample was divided into two aliquots. The first aliquot was treated according to the inventive technique, as follows:

The 10 ml aliquot was treated in vitro for three minutes with ozone gas (variable ozone concentration of 5–50 μg/ml) and ultraviolet light (253.7 nm), at a temperature of 42.5° C. An apparatus similar to that disclosed in U.S. Pat. No. 4,968,483 was utilized to carry out the treatment of the blood sample.

The second 10 ml aliquot from each sample served as an untreated control.

Platelets were isolated from the control or treated samples by centrifugation, and their ability to aggregate in response to different concentrations of ADP (a natural platelet stimulator) was measured in an aggregometer. A sample of both ozone-treated and untreated blood was used for quantitation of platelet numbers, using a Coulter counter. In some of the experiments described below, aliquots of the blood were treated with different concentrations of ozone. In other experiments performed, the blood was treated in the presence and absence of UV-light irradiation.

Platelet aggregation in the ozone-treated blood was expressed as a percentage of aggregation in the same-person untreated control blood.

Results

As shown in Table 1, the results of the experiments indicate that treatment of blood with ozone and ultraviolet light according to the invention inhibits the aggregation of blood platelets. Furthermore, there is an indication that this inhibition is dose related to the ozone concentration (see Table 2).

The effect of high levels of ozone on ADP-stimulated blood platelets

High levels of ozone (between 35 and 50 μg/ml) caused a measurable inhibition of ADP-induced platelet aggregation (arbitrarily taken as 33.3% inhibition) in 11 of the 13 experiments (8 of the 10 individuals). Taking all the data on all 10 individuals, the mean inhibition of platelet aggregation was 49.2±27.8% (mean ±sd). There was no significant difference between the inhibitory effects on blood taken from males and females (mean inhibition 48.1% and 50.7%, respectively).

This inhibition appears to relate to the concentration of ADP (aggregation stimulator) over the concentration range of 0.01–0.1 mM ADP, with lower inhibition at higher concentration of platelet agonist. However, this relationship did not hold at higher ADP concentrations (Table 1) and could be spurious, although the level of inhibition at 0.01 mM ADP is significantly greater than at 0.1 mM ADP (71% vs. 95%, p<0.02).

TABLE 1

The effect of high levels of ozone on the aggregation of
human blood platelets in the presence of varying concentrations of ADP

| Date (Individual) | Concentration of ozone (µg/ml) | Concentration of ADP (mM) | Percent Inhibition of Aggregation | Platelet Count Before Ozone/UV | After Ozone/UV |
|---|---|---|---|---|---|
| 21.11.91 (F1) | 50 | 10 | 100 | | |
| 27.11.91 (M1) | 50 | 5 | 83.3 | | |
| | | 10 | 71.4 | | |
| | | 30 | 75.0 | | |
| 2.12.91 (F2) | 50 | 10 | 0 | | |
| | | 30 | 10.0 | | |
| | | 100 | 27.3 | | |
| 3.12.91 (M2) | 50 | 0.5 | 67.1 | | |
| | | 1 | 57.1 | | |
| | | 5 | 50.0 | | |
| | | 30 | 88.1 | | |
| 6.12.91 (M3) | 50 | 0.1 | 0 | 34 | 49 |
| | | 0.1 | 6.2 | | |
| | | 0.5 | 4.0 | | |
| | | 0.5 | 0 | | |
| 11.12.91 (M4) | 50 | 0.05 | 67.0 | 46 | 93 |
| | | 0.1 | 62.4 | | |
| | | 1.0 | 74.3 | | |
| | | 10.0 | 50.0 | | |
| 12.12.91 (M5) | 50 | 0.01 | 67.0 | 51 | 121 |
| | | 0.1 | 7.1 | | |
| | | 1.0 | 35.7 | | |
| 13.12.91 (F1) | 50 | 0.01 | 63.4 | 33 | 87 |
| | | 0.05 | 22.7 | | |
| | | 0.1 | 30.4 | | |
| | | 0.5 | 15.4 | | |
| | | 1.0 | 20.8 | | |
| | | 5.0 | 20.0 | | |
| | | 10.0 | 27.6 | | |
| 9.01.92 (M6) | 50 | 0.01 | 34.2 | 34 | 40 |
| | | 0.05 | 31.0 | | |
| | | 0.1 | 9.8 | | |
| | | 0.5 | 15.4 | | |
| | | 1.0 | 26.2 | | |
| | | 5.0 | 31.3 | | |
| 10.01.92 (F3) | 50 | 0.001 | 71.4 | 49 | 64 |
| | | 0.005 | 37.5 | | |
| | | 0.01 | 69.8 | | |
| | | 0.05 | 33.8 | | |
| | | 0.1 | 31.2 | | |
| | | 0.5 | 10.1 | | |
| | | 1.0 | 21.8 | | |
| 13.01.92 (F4) | 50 | 0.005 | 100 | 49 | 52 |
| | | 0.01 | 100 | | |
| | | 0.05 | 95.2 | | |
| | | 0.1 | 92.8 | | |
| | | 0.5 | 95.9 | | |
| | | 1.0 | 91.6 | | |
| | | 5.0 | 95.8 | | |
| | | 10.0 | 80.0 | | |
| 15.01.92 (F1) | 40 | 0.01 | 90.0 | 81 | 66 |
| | | 0.05 | 71.4 | | |
| | | 0.1 | 40.7 | | |
| | | 0.5 | 87.0 | | |
| | | 1.0 | 81.8 | | |
| | | 5.0 | 95.5 | | |
| | | 10.0 | 85.2 | | |
| | | 50.0 | 84.0 | | |
| | | 100.0 | 79.1 | | |
| 21.01.92 (M2) | 35 | 0.01 | 67.1 | 68 | 79 |

The following is a summary of the data set forth in Table 1:

TABLE 1

| ADP mM | 0.01 | 0.05 | 0.10 | 0.50 | 1.00 | 5.00 | 10.0 |
|---|---|---|---|---|---|---|---|
| % inhibition of aggregation | 70.8 +/− 20.9 | 53.5 +/− 26.1 | 34.7 +/− 28.4 | 37.6 +/− 38.4 | 50.3 +/− 28.7 | 60.7 +/− 35.2 | 60.7 +/− 30.4 |
| N= | 6 | 6 | 8 | 7 | 7 | 4 | 4 |

The effect of high levels of ozone on total whole blood platelet counts

As any apparent reduction in platelet aggregation following ozone treatment of whole blood could be caused by a loss of platelets from the blood during treatment, total whole platelet counts were performed on the treated and untreated whole blood samples in 9 experiments on blood from 8 individuals. Overall, the platelet count was 115.5±59.8% of the untreated level following ozonization (range 82–264%).

Thus, the total platelet counts before and after ozone/UV treatment do not indicate a major loss of platelets from the blood as a result of ozonization.

The effect of different concentrations of ozone on the inhibition of aggregation of human blood platelets stimulated with ADP Three different concentrations of ozone (5, 25, and 50 µg/ml) were used at a range of ADP concentrations in 4 experiments on 4 different individuals. Bulking the data for different ozone concentrations from each individual and calculating the mean for the data from the 4 experiments indicated that there was some dose response relationship between the concentration of ozone used and the inhibition of platelet aggregation (see Table 2). Although overall these differences were not significant, in two of the four individuals there was a significantly greater inhibitory effect of ozone at 50 µg/ml then at 5 µg/ml (see Table 3).

TABLE 2

The effect of different concentrations of ozone on inhibition of platelet aggregation in the presence of ADP

| Date (Individual) | Concentration of ozone (µg/ml) | Concentration of ADP (mM) | Percent Inhibition of Aggregation | Platelet Count Before Ozone/UV | After Ozone/UV |
|---|---|---|---|---|---|
| 3.12.91 | 5 | 0.1 | 27.3 | | |
| (M2) | 25 | 0.1 | 100 | | |
| | 5 | 0.5 | 0 | | |
| | 25 | 0.5 | | | |
| | 50 | 0.5 | 67.1 | | |
| | 5 | 1.0 | 0 | | |
| | 25 | 1.0 | 28.6 | | |
| | 50 | 1.0 | 57.1 | | |
| | 5 | 5.0 | 0 | | |
| | 25 | 5.0 | 25.0 | | |
| | 50 | 5.0 | 50.0 | | |
| | 5 | 30.0 | 50.0 | | |
| | 25 | 30.0 | 62.0 | | |
| | 50 | 30.0 | 88.1 | | |
| 9.01.92 | 5 | 0.01 | 20.1 | 34 | 43 |
| (M6) | 25 | 0.01 | 28.9 | | 45 |
| | 50 | 0.01 | 34.2 | | 40 |
| | 5 | 0.05 | 0 | | |
| | 25 | 0.05 | 5.2 | | |
| | 50 | 0.05 | 31.0 | | |
| | 5 | 0.1 | 9.8 | | |
| | 25 | 0.1 | 1.4 | | |
| | 50 | 0.1 | 9.8 | | |
| | 5 | 0.5 | 0 | | |
| | 25 | 0.5 | 0 | | |
| | 50 | 0.5 | 15.4 | | |
| | 5 | 1.0 | 22.5 | | |
| | 25 | 1.0 | 13.7 | | |
| | 50 | 1.0 | 26.2 | | |
| | 5 | 5.0 | 0 | | |
| | 25 | 5.0 | 17.8 | | |
| | 50 | 5.0 | 31.5 | | |
| 10.01.92 | 5 | 0.001 | 57.1 | 49 | 73 |
| (F3) | 25 | 0.001 | 85.7 | | 90 |

TABLE 2-continued

The effect of different concentrations of ozone on
inhibition of platelet aggregation in the presence of ADP

| Date (Individual) | Concentration of ozone (μg/ml) | Concentration of ADP (mM) | Percent Inhibition of Aggregation | Platelet Count Before Ozone/UV–After Ozone/UV | |
|---|---|---|---|---|---|
| | 50 | 0.001 | 71.4 | | 64 |
| | 5 | 0.005 | 37.5 | | |
| | 25 | 0.005 | 80.0 | | |
| | 50 | 0.005 | 37.5 | | |
| | 5 | 0.01 | 66.4 | | |
| | 25 | 0.01 | 83.2 | | |
| | 50 | 0.01 | 69.8 | | |
| | 5 | 0.05 | 44.9 | | |
| | 25 | 0.05 | 66.9 | | |
| | 50 | 0.05 | 33.8 | | |
| | 5 | 0.1 | 29.3 | | |
| | 25 | 0.1 | 61.0 | | |
| | 50 | 0.1 | 31.2 | | |
| | 5 | 0.5 | 39.4 | | |
| | 25 | 0.5 | 54.5 | | |
| | 50 | 0.5 | 10.1 | | |
| | 5 | 1.0 | 21.8 | | |
| | 25 | 1.0 | 52.9 | | |
| | 50 | 1.0 | 21.8 | | |
| 13.01.92 (F4) | 5 | 0.005 | 100 | 49 | 60 |
| | 25 | 0.005 | 100 | | 85 |
| | 50 | 0.005 | 100 | | 52 |
| | 5 | 0.01 | 100 | | |
| | 25 | 0.01 | 87.5 | | |
| | 50 | 0.01 | 100 | | |
| | 5 | 0.05 | 84.8 | | |
| | 25 | 0.05 | 97.1 | | |
| | 50 | 0.05 | 95.2 | | |
| | 5 | 0.1 | 82.9 | | |
| | 25 | 0.1 | 91.4 | | |
| | 50 | 0.1 | 92.9 | | |
| | 5 | 0.5 | 83.3 | | |
| | 25 | 0.5 | 95.8 | | |
| | 50 | 0.5 | 95.8 | | |
| | 5 | 1.0 | 83.2 | | |
| | 25 | 1.0 | 89.5 | | |
| | 50 | 1.0 | 91.6 | | |
| | 5 | 5.0 | 79.2 | | |
| | 25 | 5.0 | 91.7 | | |
| | 50 | 5.0 | 95.8 | | |
| | 5 | 10.0 | 85.3 | | |
| | 25 | 10.0 | 80.0 | | |
| | 50 | 10.0 | 80.0 | | |

The following is a summary of the data set forth in Table 2:

| Concentration of ozone (μg/ml) | 5 | 25 | 50 |
|---|---|---|---|
| Platelet aggregation (%) (mean +/− sd, n = 4) | 38.5 +/− 30.9 | 56.5 +/− 29.4 | 55.9 +/− 26.4 |

TABLE 3

The effect of different concentrations of ozone on
inhibition of platelet aggregation in two individuals

| Concentration of ozone (μg/ml) | 5 | 25 | 50 |
|---|---|---|---|
| Platelet aggregation M2 (%) | 15.5 +/− 20.2 | 53.9 +/− 30.0 | 65.6 +/− 14.4 |
| Difference from 5 μg/ml | | ns | p < 0.01 |
| Platelet aggregation M6 | 8.7 +/− | 11.2 +/− | 24.7 +/− |
| (%) | 9.6 | 10.2 | 9.0 |
| Difference from 5 μg/ml | | ns | p < 0.02 | ns = not significant

The effect of UV light on the response of platelets to ozone

The effect of ozone on the aggregation of human blood platelets was investigated at different concentrations of ADP, in the presence or absence of UV light. The results, shown in Table 4, indicate that, although there may be some platelet aggregation-inhibitory response to ozone alone, this is nearly always greater in the presence of UV light and the effect of UV light was highly significant (p<0.001) in this single experiment. This result was also repeated in a second experiment, using a single concentration of ADP (0.01 mM). The results of this second experiment are set forth in Table 5.

TABLE 4

The effect of UV light on the inhibition of ADP-induced platelet aggregation by ozone at a concentration of 40 μg/ml. (Experiment date 15.01.92, individual F1)

| Concentration ADP (mM) | Inhibition of platelet aggregation (%) | |
| --- | --- | --- |
| | +UV | −UV |
| 0.01 | 90.0 | 60.0 |
| 0.05 | 71.4 | 0 |
| 0.1 | 40.7 | 40.7 |
| 0.5 | 87.0 | 0 |
| 1.0 | 81.8 | 0 |
| 5.0 | 95.5 | 19.4 |
| 10.0 | 85.2 | 18.5 |
| 50.0 | 84.0 | 16.0 |
| 100.0 | 79.1 | 4.2 |
| Mean +/− sd | 79.4 +/− 15.1 | 17.6 +/− 19.6 $p < 0.001$ |

TABLE 5

The effect of UV light on platelet aggregation induced by ADP (0.01 mM) in the presence or absence of ozone. (Experiment date 21.01.92, individual M2)

Percent inhibition of platelet aggregation

| Ozone 35 μg/ml + UV | Ozone 35 μg/ml − UV | No ozone, UV alone |
| --- | --- | --- |
| 83.4% | 11.2% | 0% |

In summary, the results of Example 1 indicate that the in vitro treatment of an aliquot of blood with ozone gas and ultraviolet light inhibits the aggregation of blood platelets. This platelet inhibition has been found to be dose related to the ozone concentration. Further, platelet inhibition was found to critically depend on the combined treatment of ultraviolet light and ozone gas, as evidenced in Tables 4 and 5. Treatment with ozone gas alone resulted in minimal inhibition of platelet aggregation, while treatment with ultraviolet light alone produced no inhibition of platelet aggregation.

EXAMPLE 2

Measurement of Nitric Oxide

In order to elucidate the mechanism whereby ozonization/UV light affects the aggregation of platelets in treated blood, the concentration of certain oxidized forms of nitrogen were measured.

The direct measurement of nitric oxide is difficult to achieve. However, nitric oxide is an intermediate in a metabolic pathway in which arginine is converted to citrulline. Other stable end-products are nitrates and nitrites.

Accordingly, the nitric oxide content for several samples of blood treated with ultraviolet light and ozone gas according to Example 1 were indirectly determined by measuring the combined nitrate plus nitrite concentrations in the samples before and after treatment with ozone/UV light, after converting nitrate to nitrite.

The results show that there is a small increase in nitrate plus nitrite concentrations after treatment according to the invention. This increase was consistently found in samples treated with ozone gas/UV light. Thus, nitric oxide levels may be enhanced by the treatment with ozone gas/UV light, and this may be part of the mode of action by which an inhibition of blood platelet aggregation is achieved by the invention. This therapeutic effect would be consistent with the etiology of peripheral vascular disease described above.

Conclusions

The data of Examples 1 and 2 suggest that the treatment of blood with ozone gas and ultraviolet light according to the invention is actually inducing an inhibition of platelet aggregation for the following reasons:

1. The inhibitory effect is at least partially dependent on the concentration of ADP, ozone being more inhibitory at lower ADP concentrations. This may be interpreted as the higher agonist concentrations partially overcoming the inhibitory effect of ozone by "hyperstimulating" the platelets. This suggests that the inhibition is at least partially reversible, and is probably not acting by destroying the platelet's ability to aggregate.
2. The inhibitory effect appears to be dose related to ozone concentration, with higher concentrations of ozone resulting in a greater inhibition of platelet aggregation.
3. The inhibitory effect is UV-dependent, suggesting that this is not a non-specific toxic effect caused by the oxidative capacity of the ozone gas.

EXAMPLE 3

Measurement of Prostacyclin

In order to assess the effect of treatment of blood with UV/ozone according to the invention on blood levels of prostacyclin, the concentration of its stable metabolite, 6-keto prostaglandin-F1-alpha, was measured.

Samples of blood from eight individuals were divided into two aliquots, one of which was treated with UV/ozone as described in Example 1, the other aliquot serving as an untreated control. The level of 6-keto prostaglandin-F1-alpha was then measured for each blood sample using standard techniques. The results are as follows:

| Individual | Plasma 6-keto PGF1-alpha conc. | | Percent Increase |
| --- | --- | --- | --- |
| | Control | Ozone/UV Treated | |
| 1 | 2.0 | 4.6 | 230 |
| 2 | 1.7 | 8.8 | 518 |
| 3 | 1.2 | 5.7 | 475 |
| 4 | 0.6 | 2.7 | 450 |
| 5 | 2.7 | 6.7 | 248 |
| 6 | 2.3 | 2.0 | 87 |
| 7 | 2.6 | 4.0 | 154 |
| 8 | 3.1 | 8.0 | 258 |
| | | Mean | 303% |

Thus, in seven out of the eight individuals, treatment of their blood with UV/ozone resulted in an increase in the concentration of the prostacyclin metabolite, suggesting that this may be an additional mechanism whereby the treatment of the invention works to treat peripheral vascular disease and other diseases associated with blood platelet aggregation.

EXAMPLE 4

Proliferation of Peripheral Blood Mononuclear Cells

This example illustrates the immune-stimulatory effect on blood which results from treatment of the blood with UV/ozone according to the invention.

Whole blood from four individuals was exposed to UV/ozone treatment as described in Example 1, using ozone concentrations ranging from about 35 µg/ml to 50 µg/ml. A parallel control of blood from the same person was treated with oxygen alone (no ozone/UV).

Peripheral blood mononuclear cells (PBMCs; a mixture of T-lymphocytes and monocytic cells) were isolated from each sample of blood by gradient density centrifugation. The isolated PBMCs were then cultured in the presence of Interleukin-2 as a stimulator. After three days of culture, the proliferation of the cells was assessed by measuring the incorporation of tritiated thymidine into the DNA of the dividing cells. The results are as follows:

| Indi- | Uptake of tritiated thymidine (cpm, mean +/– sd) | | Percent Stimulated |
|---|---|---|---|
| vidual | Control | Ozone/UV Treated | by Ozone/UV |
| 1 | 1433 +/– 368 | 4195 +/– 606 | 293 |
| 2 | 427 +/– 111 | 1238 +/– 166 | 290 |
|   | 484 +/– 88 | 1340 +/– 165 | 277 |
| 3 | 299 +/– 64 | 837 (mean of 2) | 280 |
|   | 437 (n = 2) | 1351 (n = 2) | 309 |
| 4 | 9102 +/– 889 | 5311 +/– 1601 | 58 |
|   | 9485 +/– 1483 | 5050 +/– 1332 | 53 |

In conclusion, in three of the four individuals, treatment of their blood with UV/ozone according to the invention increased the proliferation of peripheral blood mononuclear cells after stimulation by Interleukin-2. Thus, the treatment of the invention has an immune-stimulatory effect on blood.

EXAMPLE 5

Staining of Activation Markers

This example illustrates a second experimental approach which indicates that treatment of blood with UV/ozone according to the invention has an immune-stimulatory effect on human blood.

Samples of blood were separated into aliquots, in which one group of aliquots were treated with UV/ozone as described in Example 1, and the other group of samples were maintained as an untreated control. Each blood sample was then stained for certain activation markers of T-lymphocytes and monocytes, using conventional monoclonal antibody techniques. The proportion of the total cells which stained positive for the individual markers was quantitated by microscopy, The results are as follows:

| Marker | Control | Ozone/UV Treated |
|---|---|---|
| CD25 (IL-2 receptor) | 1% | 26% |
| CD2 (E-rosette receptor) | 3% | 33% |
| HLA-DR (monocyte activation) | 0% | 2% |

The above data for this example are all means of duplicates, and indicate that treatment with UV/ozone according to the invention results in the stimulation of T-lymphocytes and monocytes, further supporting the data in Example 4 above.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A method of treating Raynaud's Disease in a human patient with Raynaud's Disease, which comprises:

selecting an aliquot of from about 0.01 ml to about 400 ml of human blood of a type compatible with the blood of a human patient with Raynaud's Disease;

contacting the selected blood aliquot simultaneously with a blood platelet aggregation-inhibiting effective amount of ozone gas in admixture with oxygen gas, and ultraviolet radiation, while maintained at a temperature in the range from about 37° C. to about 43° C. for a period for about 0.5 minutes to about 10 minutes;

and administering the blood aliquot so treated to the human patient with Raynaud's Disease.

2. The method of claim 1 wherein the ozone gas is at a concentration of 0.5 micrograms per ml to about 100 micrograms per ml.

3. The method of claim 1 wherein the ozone gas is at a concentration from about 5 micrograms per ml to about 50 micrograms per ml.

4. The method of claim 1 wherein the ultraviolet radiation has a wavelength of about 253.7 nm.

5. The method of claim 1 wherein the blood aliquot is maintained at a temperature of about 42.5° C. while being contacted with the ozone gas in admixture with the oxygen gas, and ultraviolet radiation.

6. The method of claim 1 wherein the blood aliquot has a volume of about 10 ml.

7. The method of claim 1 wherein time blood aliquot is contacted with the ozone gas in admixture with oxygen gas and ultraviolet radiation for a period of about 3 minutes.

8. The method of claim 1 wherein the blood aliquot is administered to the human patient with Raynaud's Disease by a method selected from the group consisting of interarterial injection, intramuscular injection, intravenous injection, sub-cutaneous injection, and intraperitonial injection.

9. The method of claim 1 wherein the blood aliquot is obtained by removing the blood aliquot from the same human to whom the blood is administered after treatment of the blood aliquot.

* * * * *